United States Patent [19]
Mourkidou

[11] Patent Number: 5,695,454
[45] Date of Patent: Dec. 9, 1997

[54] COVER FOR A LARYNGOSCOPE

[76] Inventor: Sotiria Mourkidou, P.O. Box 366, Malibu, Calif. 90265

[21] Appl. No.: 394,367

[22] Filed: Feb. 24, 1995

Related U.S. Application Data

[63] Continuation-in-part of Ser. No. 268,329, Jun. 30, 1994, abandoned.

[51] Int. Cl.$^6$ ............................................. A61B 1/26
[52] U.S. Cl. ........................... 600/166; 600/165; 600/190; 600/191; 600/203; 600/121
[58] Field of Search ......................... 600/185, 186, 600/190, 197, 198, 203, 206, 121, 122, 124; 206/438, 363, 366, 370; 383/15, 16, 907

[56]  References Cited

U.S. PATENT DOCUMENTS

| | | | |
|---|---|---|---|
| 4,953,567 | 9/1990 | Ward | 383/907 X |
| 4,972,825 | 11/1990 | Vescovo, Jr. | 600/186 |
| 5,003,963 | 4/1991 | Bullard et al. | 600/185 X |
| 5,168,863 | 12/1992 | Kurtzer | 600/122 |
| 5,337,734 | 8/1994 | Saab | 128/4 |
| 5,347,995 | 9/1994 | Slater et al. | |
| 5,406,939 | 4/1995 | Bala | 600/121 |

OTHER PUBLICATIONS

"A simple, cost-effective method of preventing laryngoscope handle contamination", *Anesthesiology*, V82, No. 3, Mar. 1995, p. 790.

*Primary Examiner*—Beverly M. Flanagan
*Attorney, Agent, or Firm*—Merchant, Gould, Smith, Edell, Welter & Schmidt

[57]  ABSTRACT

A cover for a laryngoscope which includes a generally elongated cylindrical handle, a branch member and an insertion member. The cover generally comprises an end sheath, a Y-branch portion connected to the end sheath and two cylindrical sleeves connected to the Y-branch portion. The tapered sheath covers the insertion member and has a closed end. The Y-branch portion covers an area adjacent the joint between the handle and the branch member and preferably comprises an expandable structure. Each of the cylindrical sleeve covers the handle and the branch member, respectively. As a result, the laryngoscope itself is shielded from the contact with the interior of the mouth and the larynx. Once the cover is used, the cover may be discarded. Accordingly, cleaning and sterilization of the laryngoscope are substantially facilitated and hygienic operation of the laryngoscope is improved.

20 Claims, 8 Drawing Sheets

COVER FOR A LARYNGOSCOPE

The present application is a continuation-in-part of U.S. application Ser. No. 08/268,329, filed Jun. 30, 1994, now abandoned.

BACKGROUND OF THE INVENTION

1. Field of the Invention

This invention relates to a cover for a laryngoscope that is inserted into the larynx through the mouth and used for observing the interior of the larynx, for example, to assist a medical practitioner to insert one or more tubes into a canal leading to a patient's lung.

2. Description of Related Art

The larynx is a part of the respiratory tract extending from the pharynx (throat) to the trachea (windpipe), having walls of cartilage and muscle and containing the vocal cords enveloped in folds of mucous membrane. The larynx of a person has a flap like structure at its inlet which is called the epiglottis. The epiglottis allows swallowed food to pass from the throat into the esophagus rather than into the trachea. The larynx contains the vocal cords, which produce sound that is converted into speech by the lips, teeth, and tongue. The vocal cords, located in the upper region of the larynx, are two muscularized folds of mucous membrane that extend from the larynx wall. The gap between the folds is the glottis. Each fold encloses an elastic vocal ligament and muscle, which controls the tension and rate of vibration of the cords as air passes through them. In normal breathing the vocal muscles are held slack, allowing air to pass in and out of a wide slit.

When cancers or other abnormalities are developed interior of the larynx, for example at the vocal cords, the abnormality may be observed by using an imaging apparatus, such as a CT (computed tomography) apparatus or an MRI (magnetic resonance imaging) apparatus. When a biopsy or more careful evaluation of the abnormalities is needed, direct laryngoscopy is typically carried out to enable first-hand observation of the abnormalities. Viewing of the interior of the larynx may be carried out for other purposes as well.

Direct laryngoscopy involves the use of a flexible laryngoscope which is inserted into the larynx through the nostril or a rigid laryngoscope which is inserted into the larynx through the mouth. A typical rigid laryngoscope has a handle and body connected to an insertion member, typically formed as a beak-like tapered end portion. The handle or body and the beak-like tapered end portion may be foldably connected to each other by a joint so that the beak-like tapered end portion and the handle are opened and closed with respect to each other about the joint. The beak-like tapered end portion is designed to be inserted through the patient's mouth and has a curved surface for holding down the tongue while the tapered end portion is inserted into the interior of the larynx. The tapered end portion is provided with a light source to irradiate the interior of the larynx to allow visual examination of the interior of the larynx. A laryngoscope of this type is generally made of metal and can be repeatedly reused as long as suitable cleaning and sterilization steps are taken between each use. However, because of the folding structure and the small crevices, gaps, openings and sharp corners, typically present around the pivot joint, thorough cleaning and sterilization of the laryngoscope are relatively difficult and time-consuming. If the laryngoscope is not thoroughly sterilized, the use of the imperfectly sterilized laryngoscope may pose serious hygiene problems.

Some laryngoscopes are provided with one or more additional branch members extending from the body, handle or beak-like tapered end portion, through which an optical endoscope, for example, may be inserted to allow visual examination of the interior of the larynx. Such branch members typically extend from a location adjacent an area between the handle and the beak-like tapered end portion so that the three members, namely, the handle, each branch member and the beak-like tapered end portion generally define a shape of letter the Y. Still other laryngoscopes are provided with one or more branch portions which are used, for example, as a suction port to permit removal of fluids or delivery of gases or other fluids. Laryngoscopes having such additional branch portions likewise may be repeatedly reused as long as suitable cleaning and sterilization steps are taken between each use. However, the branch structure (and the sharp angles defined by such structures) typically makes thorough cleaning and sterilization of the laryngoscope relatively difficult and time-consuming.

SUMMARY OF THE DISCLOSURE

It is an object of embodiments of the present invention to facilitate cleaning and sterilization of a laryngoscope.

It is another object of embodiments of the present invention to improve the hygienic operation of a laryngoscope having branch members such as suction pods, optical endoscope ports, etc.

These and other objects and advantages are achieved, in accordance with one embodiment of the present invention, in a cover for a laryngoscope which includes a generally elongated cylindrical handle, a branch member and an insertion member. According to a preferred embodiment, a cover generally comprises a tapered sheath, a Y-branch portion connected to the tapered sheath and two cylindrical sleeves connected to the Y-branch portion. The tapered sheath portion covers the insertion member and has a closed end. The Y-branch portion covers an area adjacent the joint between the handle and the branch member and preferably comprises an expandable structure. Each of the cylindrical sleeve portions covers the handle and the branch portion, respectively. As a result, the laryngoscope itself is shielded from direct contact with the interior of the mouth and the larynx. Once the cover is used, the cover may be removed from the laryngoscope and discarded. Accordingly, cleaning and sterilization of the laryngoscope are substantially facilitated and hygienic and safe environments in the operation of the laryngoscope are improved.

Also, because laryngoscopes typically employ optical devices or light emitting devices on or around the beak-like tapered end portions, the cover in preferred embodiments is made from a material suitable for light passage therethrough with minimum optical distortion. In preferred embodiments, the cover is made from a polyurethane or EMA material, as such a material can be made suitably thin (e.g. at a thickness in the range of 1-2 mil.) and suitably transparent to light passage, yet maintain suitable structural strength.

DETAILED DESCRIPTION OF PREFERRED EMBODIMENT

While embodiments of the present invention may be configured to operate with various types of laryngoscopes, for purposes of simplifying the present disclosure, cover embodiments are described with reference to laryngoscopes of the type shown in FIGS. 1–5.

Figure 1:
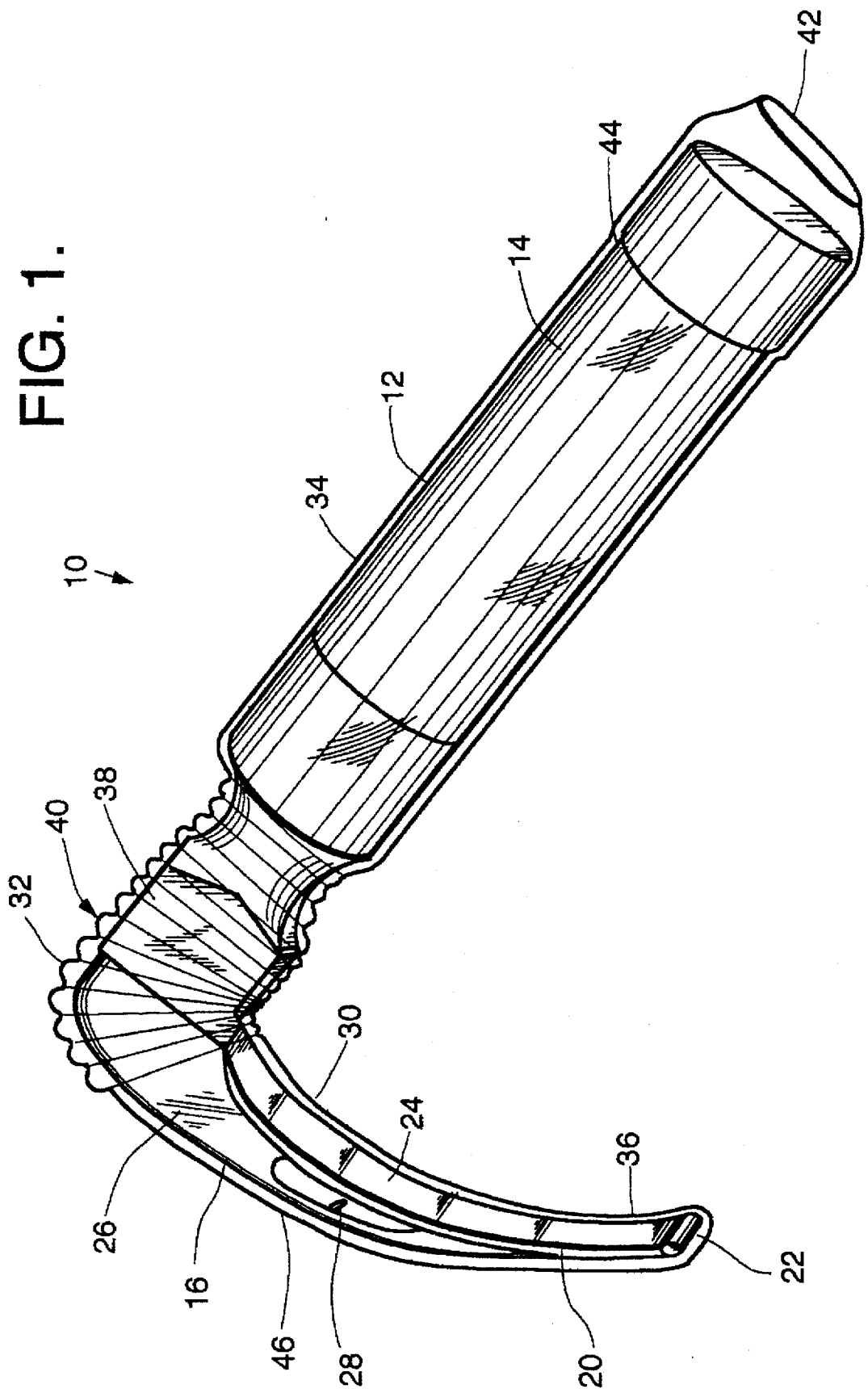
FIG. 1 is a perspective view of a laryngoscope in an open position and a cover covering substantially the entire external surface of the laryngoscope in accordance with a preferred embodiment of the present invention.
Figure 2:
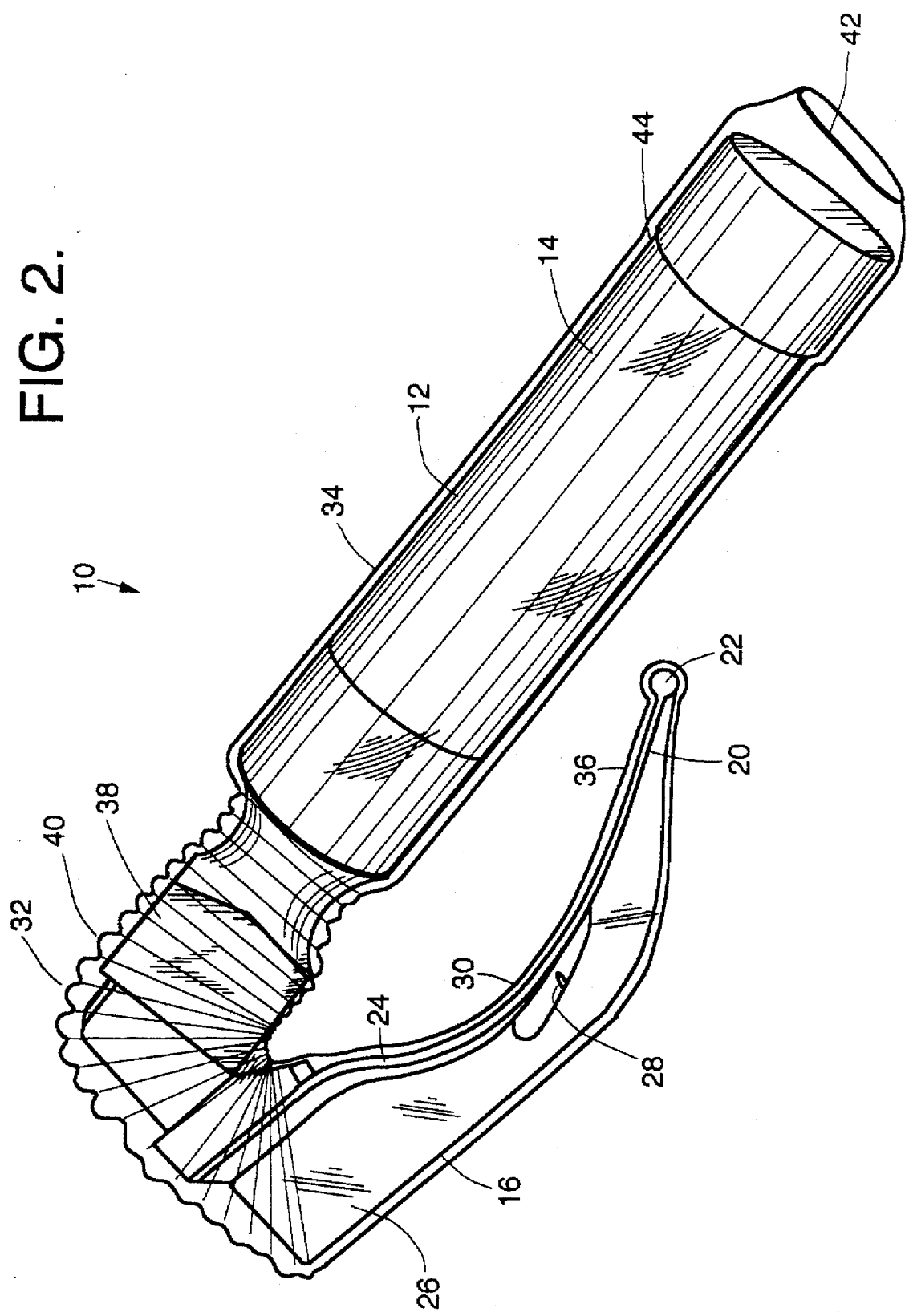
FIG. 2 is a perspective view of the laryngoscope in a closed position and the cover shown in FIG. 1.

A laryngoscope cover in accordance with a preferred embodiment is indicated generally at 10 in FIGS. 1 and 2. The cover 10 is pulled over a typical laryngoscope 12. The laryngoscope 12, as shown in FIG. 1, has a cylindrical handle 14 and a beak-like insertion member 16. As best seen in FIG. 2, the cylindrical handle 14 and the beak-like insertion member 16 are connected to each other by a joint assembly 18.

The insertion member 16 pivots about the joint assembly 18 between a fully open position and a fully closed position. The insertion member 16 can be pivoted with respect to the handle 14 to the fully open position at which the insertion member 16 is generally perpendicular to the handle 14, as best shown in FIG. 1. Also, the insertion member 16 can be pivoted with respect to the handle 14 to the fully closed position at which the insertion member 16 is generally in parallel with the handle 14, as shown in FIG. 2. When the laryngoscope 12 is used for examination of the interior of the larynx, the insertion member 16 may be pivoted to a desired angle with respect to the handle 14, for example, to the fully open position or to a position between the fully opened and fully closed positions.

The insertion member 16 has a tapered end portion 20 which is curved toward the end 22 of the insertion member 16. The insertion member 16 is also provided with a gently curved bottom surface 24 which is adapted to press against the tongue of a patient. A curved ridge member 26 is attached to the curved bottom surface 24 to improve the structural rigidity of the insertion member 16. The insertion member 16 also has a light source 28 mounted in the curved ridge member 26 for illuminating the interior of the larynx.

In one embodiment, the cover 10 encloses substantially the entire surface of the laryngoscope and is shaped to substantially conform to the external surface contour of the laryngoscope 12. In another embodiment, the cover 10 may be designed to have a size slightly larger than the laryngoscope to facilitate the insertion of the laryngoscope into the cover 10. The cover 10 is preferably made of a suitable hygienic, flexible or elastic material. Materials, such as, for example, latex, synthetic rubber or plastic, have been used for gloves or prior covers used in the medical profession. However, the present inventor has found that polyurethane or ethyl methyl acrylic (EMA) material can be formed suitably thin and transparent to provide improved light transmissivity and optical clarity, while maintaining sufficient strength and flexibility characteristics. Therefore, preferred embodiments are formed of a generally thin, transparent polyurethane material having a thickness of within the range of about 1 mil. and about 2 mil. Such a thickness of polyurethane material has been found to provide good optical clarity and light transmissivity, yet be suitably strong and flexible for covering a typical laryngoscope.

The cover 10 comprises a unitary structure having generally three segments: a tapered end sheath 30, a flexible elbow 32, and a cylindrical sleeve 34. The tapered end sheath 30 substantially covers the insertion member 16 and has a closed end portion 36 which is shaped to substantially conform to the exterior surface of the tapered end portion 20.

The flexible elbow 32 connects to the tapered end sheath 30. In a preferred embodiment, the flexible elbow 32 comprises bellows 38. In another embodiment, the elbow 32 is made from a substantially elastic material. It is appreciated that the length of an exterior area 40 about the joint assembly 18 substantially changes according to the bent angle between the insertion member 16 and the handle 14. The bellows 38 provides and stores slack for accommodating changes in the length of the exterior area 40 at the elbow 32. As a result, the bending movement is facilitated and the area adjacent the elbow 32 is strengthened. Other suitable structure (such as circumferential ribs) may be provided at the elbow for facilitating flexibility. The elbow 32 connects to the cylindrical sleeve 34 which covers substantially the entire surface of the handle 14. The cylindrical sleeve 34 is terminated with an opening 42. The laryngoscope 12 is inserted into the cover 10 through the opening 42.

FIG. 1 shows a gap (44, 46) between the external surface of the handle 14 and the cylindrical sleeve 34, and between the external surface of the insertion member 16 and the tapered end sheath 30. In one embodiment, each of the segments of the cover 10 may be made of an elastic material and is designed to have a size slightly smaller than each of the segments of the laryngoscope so that the cover stretches to cover the laryngoscope and elastically and tightly fits to the external surface of the laryngoscope. However, in preferred embodiments, each of the segments of the cover 10 is made of a material having a suitable flexibility and elasticity and a size slightly larger than at least the handle 14 of the laryngoscope. This feature facilitates quick and easy insertion of the laryngoscope into the cover 10.

As described above, the insertion member 16 is provided with a lighting source 28 for illuminating the interior of the larynx. Therefore, at least a portion of the tapered end sheath 30 which covers over the light source 28 should be formed from a substantially transparent material to allow the light to pass through the sheath 30. Alternatively, the entire cover 10 may be formed from a substantially transparent material, preferably, for example, transparent polyurethane or EMA. As discussed above, it has been found that a relatively thin cover may be made from polyurethane or EMA which has an improved light transmissivity and a minimal optical distortion.

Figure 3:
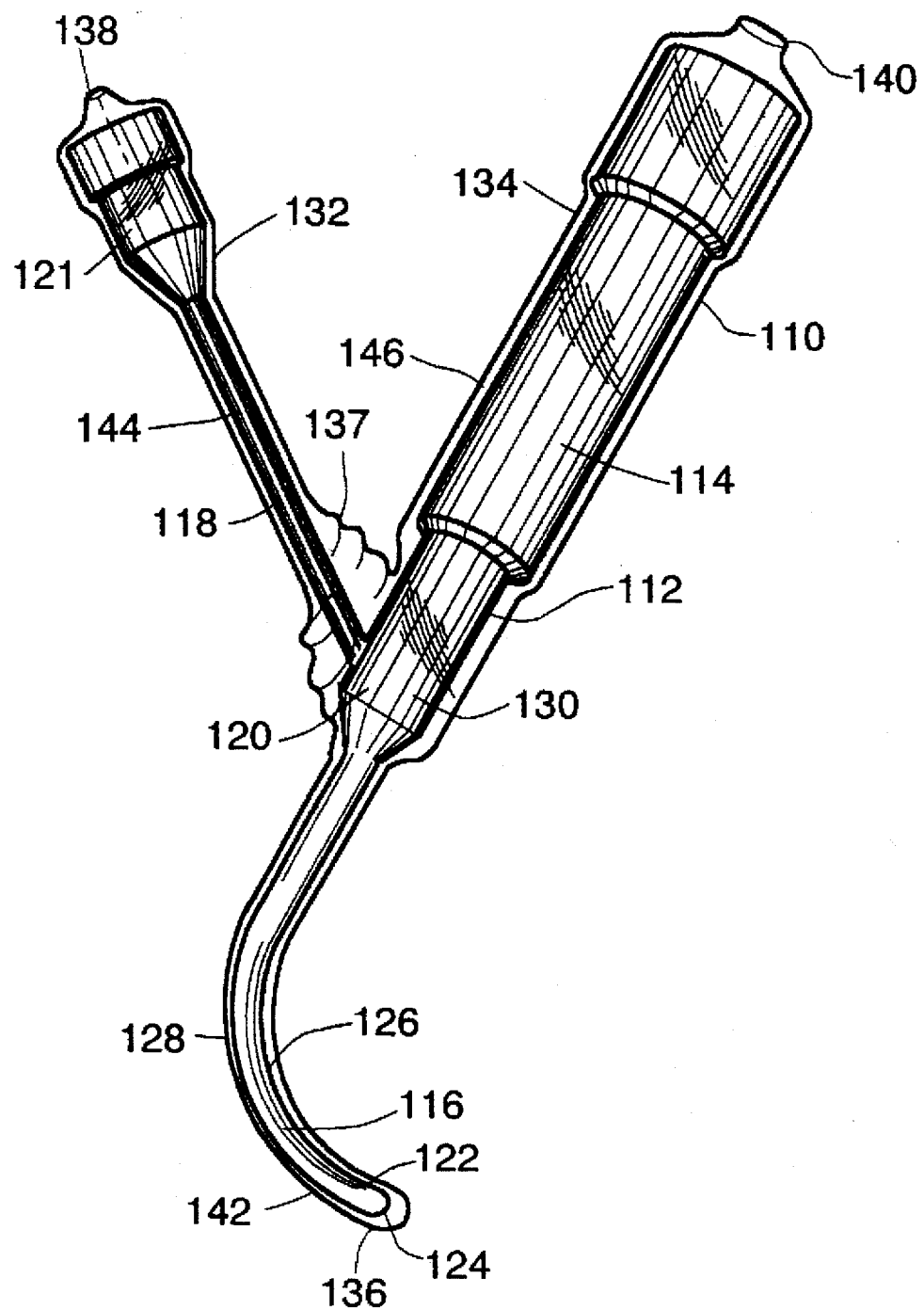
FIG. 3 is a perspective view of a laryngoscope with an optical endoscope port branching out from the handle of the laryngoscope and a cover covering substantially the entire external surface of the laryngoscope in accordance with a preferred embodiment of the present invention.

A laryngoscope cover in accordance with another preferred embodiment is indicated generally at 110 in FIG. 3. The cover 110 is pulled over a laryngoscope 112. The laryngoscope 112, as shown in FIG. 3, has a cylindrical handle 114 and a beak-like insertion member 116. In the illustrated embodiment, the laryngoscope 112 has a branch member 118 which branches out from an area 120 adjacent the joint between the handle 114 and the beak-like insertion member 116. In one embodiment, the branch member 118 defines an eyepiece 121. As shown in FIG. 3, the cylindrical handle 114, the beak-like insertion member 116 and the branch member 118 generally define the shape of letter Y.

The insertion member 116 has an end portion 122 which is curved toward an end portion 124 of the insertion member 116. The insertion member 116 is also provided with a gently curved bottom surface 126 which is adapted to press against the tongue of a patient.

In one embodiment, the cover 110 encloses substantially the entire surface of the laryngoscope 112 and is shaped to substantially conform to the external surface contour of the laryngoscope 112. In an alternative embodiment, the cover 110 is shaped to relatively loosely fit to the external surface of the laryngoscope 112. Such a loosely fit cover 110 can be quickly and easily installed on and removed from the laryngoscope 112. The ability to quickly and easily install or remove a cover from a laryngoscope is beneficial (or necessary), particularly in an emergency situation when the doctor has little time to prepare for the insertion of the laryngoscope. The cover 110 is preferably made of a suitable hygienic, flexible or elastic material, preferably, polyurethane or EMA. In a preferred embodiment, the cover 110 is made from a material having an improved light transmissivity and minimal optical distortion for scopic operations. It has been discovered that polyurethane or EMA can be made thin enough to have improved light and optical transmissivity and is still strong. When a film or sheet of polyurethane or EMA is made into a thickness in the range between about 1 mil. and about 2 mil., the film or sheet of polyurethane or EMA has an improved light transmissivity and exhibits a minimal optical distortion. Furthermore, polyurethane and, especially EMA, can be relatively inexpensive and readily applicable to manufacturing processes.

The cover 110 comprises a unitary structure having generally four segments: an end sheath 128, a Y-shaped branch portion 130, a first cylindrical sleeve 132 and a second cylindrical sleeve 134. In preferred embodiments, each of the first cylindrical sleeve 132 and the second cylindrical sleeve 134 has a length longer than the length of the branch member 118 and the length of the handle 114, respectively, to maximize coverage on most handle sizes without increasing installation difficulty or manufacturing cost.

The tapered end sheath 128 substantially covers the insertion member 116 and has a closed end portion 136 which is shaped to substantially conform to the exterior surface of the end portion 124.

The Y-shaped branch portion 130 connects to the end sheath 128. In a preferred embodiment, the Y-shaped branch portion 130 comprises a bellows-like structure 137. In another embodiment, the Y-shaped branch portion 130 is made from a substantially flexible material. As described later in greater detail, the first cylindrical sleeve 132 may be substantially extended away from the laryngoscope 112 when the branch member 118 is inserted into the first cylindrical sleeve 132. The bellows-like structure 137 provides and stores slack for accommodating changes in the length of the first cylindrical sleeve 132.

The Y-shaped branch portion 130 connects to the first cylindrical sleeve 132 which covers substantially the entire surface of the branch member 118 including the eyepiece 121. The first cylindrical sleeve 132 is terminated with an opening 138 to allow connection of external equipments, such as, for example, teaching attachment or video equipment. The Y-shaped branch portion 130 also connects to the second cylindrical sleeve 134 which covers substantially the entire surface of the handle 114. The second cylindrical sleeve 134 is terminated with an opening 140. The laryngoscope 112 is inserted into the cover 110 through the opening 140.

FIG. 3 shows a gap (142, 144, 146) between the external surface of the insertion member 116 and the end sheath 128, between the branch member 118 and the first cylindrical sleeve 132, and between the external surface of the handle 114 and the second cylindrical sleeve 134. As discussed in greater detail later, when the laryngoscope 112 is inserted within the cover 110, the second cylindrical sleeve 134 may be substantially extended laterally with respect to the handle 114 so that the second cylindrical sleeve 134 passes over the branch member 118. Therefore, in a preferred embodiment, the second cylindrical sleeve 134 may be relatively large in size as compared with the size of the handle 114 to facilitate stretching of the second cylindrical sleeve 134. Preferably, the second cylindrical sleeve 134 is made from flexible, transparent polyurethane or EMA material. The bellows-like structure 137 may be provided with the second cylindrical sleeve 134 to facilitate the extension of the second cylindrical sleeve 134.

The laryngoscope 110 may be provided with a light source (not shown) adjacent the end portion 124 to illuminate the interior of the larynx. Therefore, at least a portion of the end sheath 128 which covers over the insertion member 116 should be formed from a substantially transparent material to allow the light to pass through the sheath 128. Alternatively, the entire cover 110 may be formed from a substantially transparent material, preferably, transparent polyurethane or EMA. In a preferred embodiment, the entire cover 110 or at least the portion of the end sheath 128 is formed from polyurethane or EMA having an appropriate thickness designed to provide an improved light transmissivity and minimal optical distortion.

Figure 4:
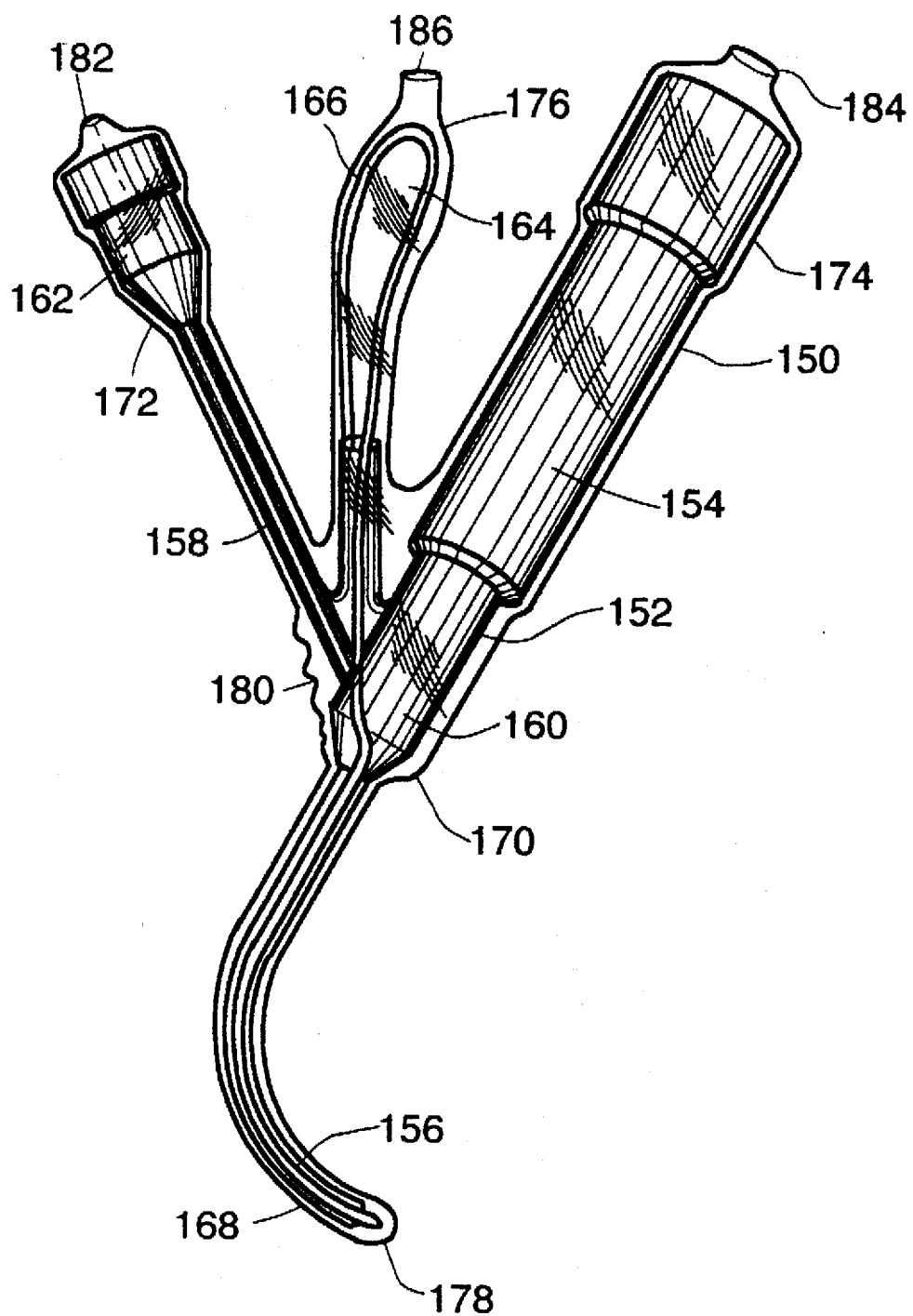
FIG. 4 is a perspective view of a laryngoscope with an optical endoscope port and a suction port both branching out from the handle of the laryngoscope and a cover covering substantially the entire external surface of the laryngoscope in accordance with another preferred embodiment of the present invention.

A laryngoscope cover in accordance with another preferred embodiment is indicated generally at 150 in FIG. 4. The cover 150 is pulled over a laryngoscope 152. The laryngoscope 152, as shown in FIG. 4, has generally similar components and structure as the one shown in FIG. 3 except that the laryngoscope 152 has a plurality of branch members. More specifically, the laryngoscope 152 has a cylindrical handle 154 and a beak-like insertion member 156. In the illustrated embodiment, the laryngoscope 152 has a first branch member 158 which branches out from an area 160 adjacent the joint between the handle 154 and the beak-like insertion member 156. In one embodiment, the first branch member 158 comprises an eyepiece port 162. In this embodiment, the laryngoscope 152 has a second branch member 164 which comprises, for example, a introducing stylet 166.

In one embodiment, the cover 150 encloses substantially the entire surface of the laryngoscope 152 and is shaped to substantially conform to the external surface contour of the laryngoscope 152. The cover 150 is preferably made of a suitable hygienic, flexible material, preferably polyurethane or EMA.

The cover 150 comprises a unitary structure having generally five segments: an end sheath 168, a branch portion 170, a first sleeve 172, a second sleeve 174, and a third sleeve 176. The end sheath 168 substantially covers the insertion member 156 and has a closed end portion 178. The branch portion 170 connects to the end sheath 168. In a preferred embodiment, the branch portion 170 comprises a bellows-like structure 180. In another embodiment, the branch portion 170 is made from a substantially flexible material in order to facilitate substantial extension of the branch portion 170.

The branch portion 170 connects to the first sleeve 172 which covers substantially the entire surface of the first branch member 158 including the eyepiece 162. The first sleeve 172 is terminated with an opening 182 to allow connection of external equipments, such as, for example, teaching attachment or video equipment. The branch portion 170 also connects to the second sleeve 174 which covers substantially the entire surface of the handle 154. The second sleeve 174 is terminated with an opening 184 through which the laryngoscope 152 is inserted into the cover 150. The branch portion 170 further connects to the third sleeve 176 which covers substantially the entire surface of the second branch member 164. The third sleeve 176 may be terminated with an opening 186. Alternatively, the third sleeve 176 may have a closed end (not shown).

Figure 5:
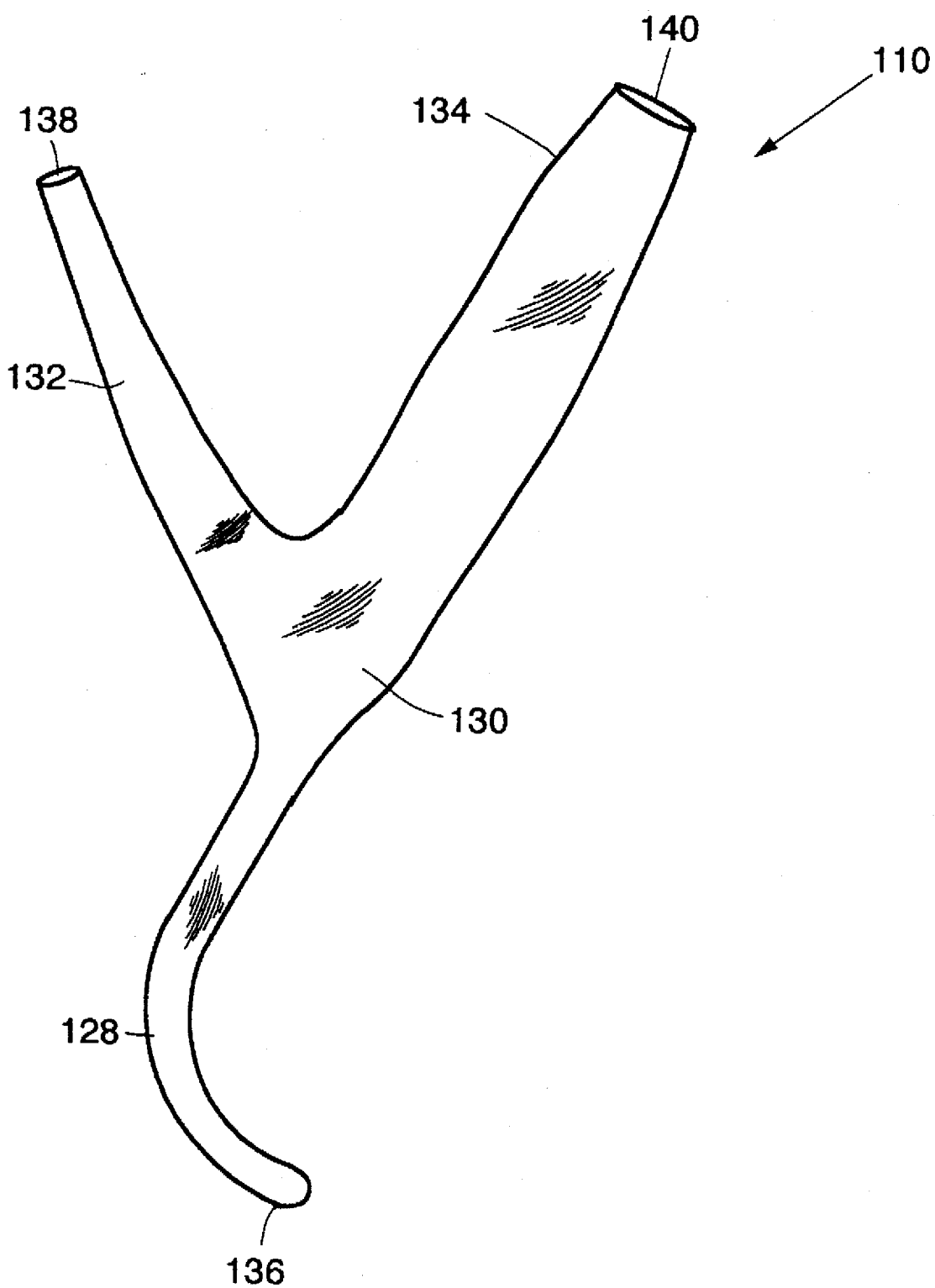
FIG. 5 is a perspective view of a laryngoscope cover which is used for the laryngoscope shown in FIG. 3.

Referring to FIGS. 5-8, one exemplary method of covering the laryngoscope 112 with the cover 110 will be described. FIG. 5 shows the cover 110 having the end sheath 128, the Y-shaped branch portion 130, the first cylindrical sleeve 132 and the second cylindrical sleeve 134. The end sheath 128 has the closed end portion. The first cylindrical sleeve 132 and the second cylindrical sleeve 134 define the openings 138 and 140, respectively.

Figure 6:
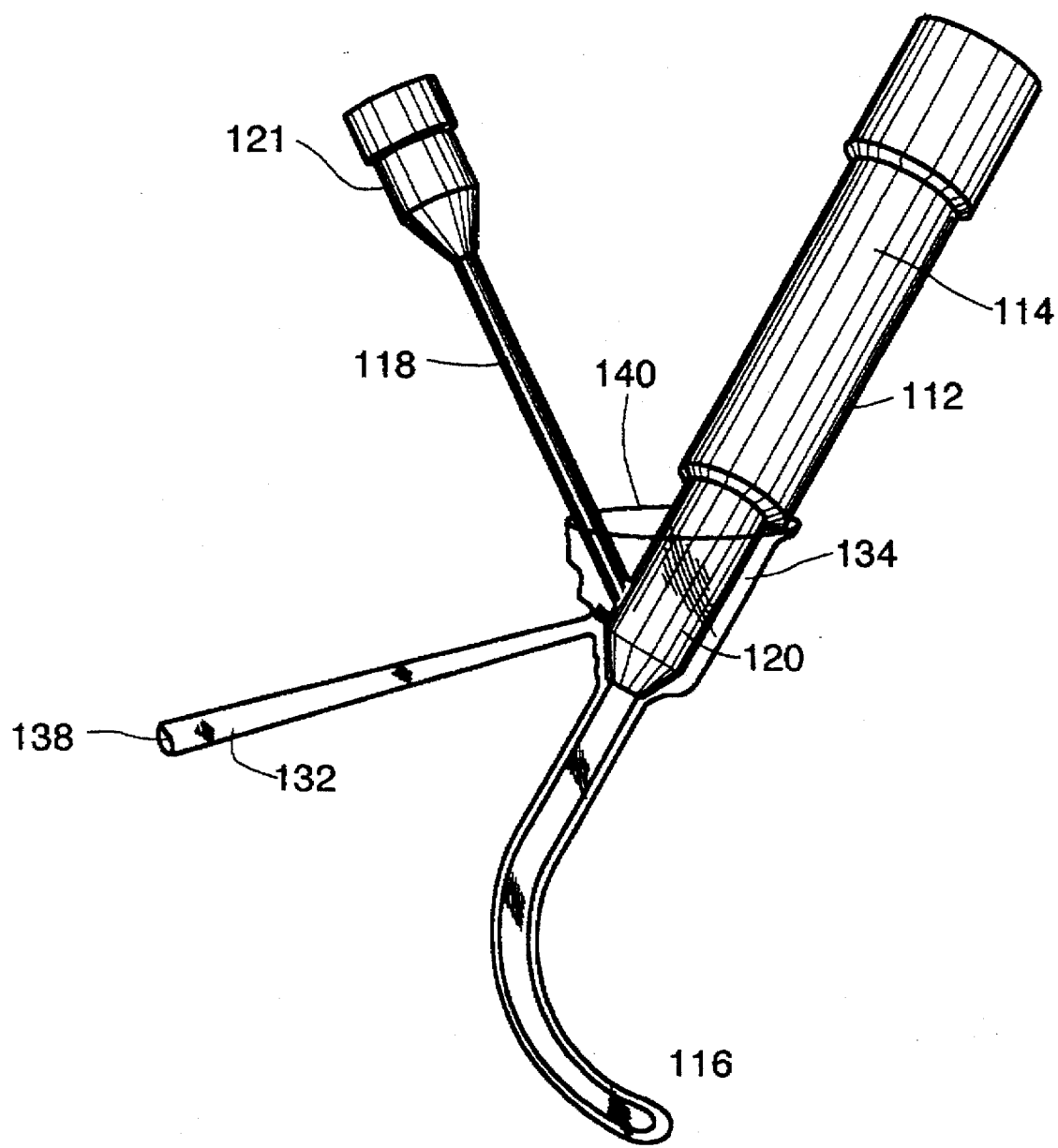
FIGS. 6–8 are explanatory views illustrating a method for covering the laryngoscope shown in FIG. 3 with the cover shown in FIG. 5, in accordance with one embodiment of the present invention.
Figure 7:
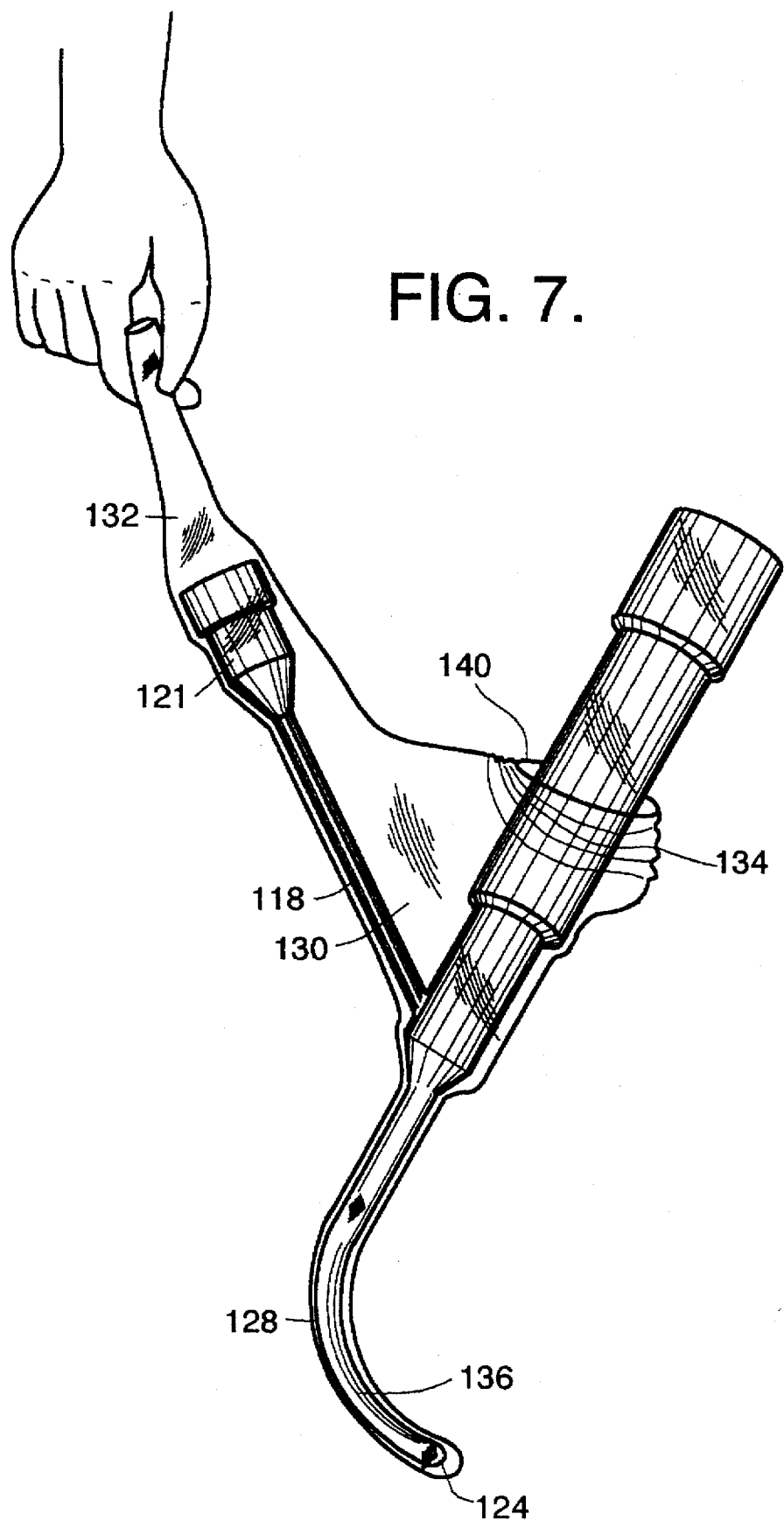

First, the insertion member 116 of the laryngoscope 112 is inserted through the opening 140 of the cover 110 and placed within the end sheath 128, as shown in FIG. 6. Then, the opening 140 of the second cylindrical sleeve 134 is stretched to pass over the branch member 118 and the eyepiece 121. When the opening 140 has passed the branch member 118 and the eyepiece 121, the Y-shaped branch portion 130 or the first cylindrical sleeve 132 with the Y-shaped branch portion 130 may be stretched to allow insertion of the branch member 118 and the eyepiece 121 into the first cylindrical sleeve 132, as shown in FIG. 7. In a preferred embodiment, the cover 110 including the second cylindrical sleeve 134 is made from a polyurethane or EMA material that has a suitable flexibility. The bellows-like structure 137 may be provided adjacent the Y-shaped branch portion 130 to facilitate the extension of the second cylindrical sleeve 134. In a preferred embodiment, the end sheath 128 is made from a polyurethane or EMA material having a thickness in the range between about 1 mil. and about 2 mil. to provide an improved light transmissivity and minimal optical distortion.

Figure 8:
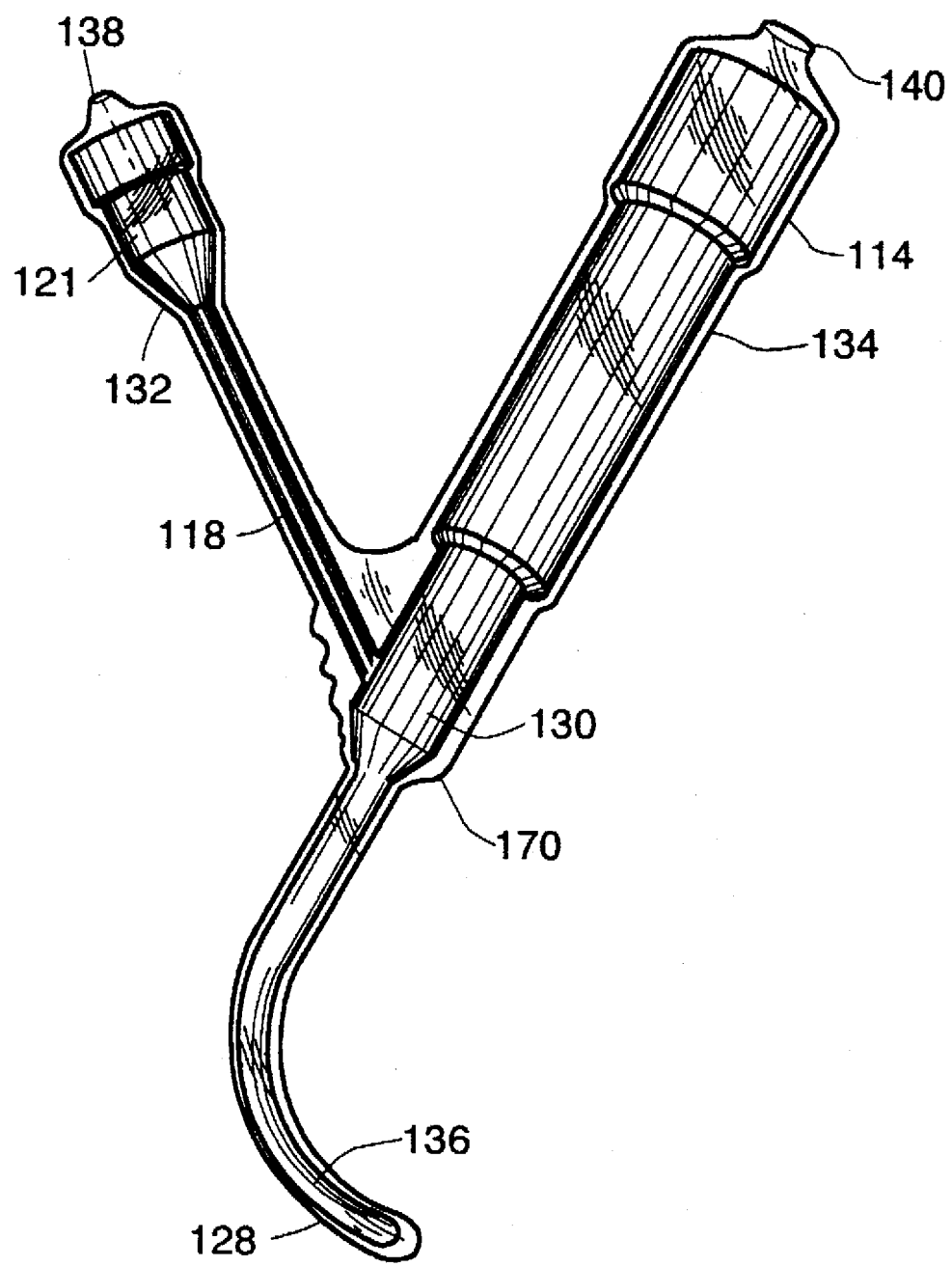

When the branch member 118 together with the eyepiece 121 are placed within the first cylindrical sleeve 132, the second cylindrical sleeve 134 is pulled over the handle 114, as shown in FIG. 8.

The laryngoscope 152 shown in FIG. 4 may be covered with the cover 150 in a similar manner. More specifically, the insertion member 156 of the laryngoscope 152 is inserted through the opening 184 of the cover 150 and placed within the end sheath 168. Then, the opening 184 of the second cylindrical sleeve 174 is stretched over the first branch member 158 and the second branch member 164. When the opening 140 has passed these components, the second branch member 176 is inserted into the third sleeve 176, and the first branch member 158 is inserted into the first sleeve 172. Thereafter, the second sleeve 174 is pulled over the handle 154.

The presently disclosed embodiments are to be considered in all respects as illustrative and not restrictive. For example, for a laryngoscope having more than two branch members, a cover may have more than two sleeves for covering the corresponding number of the branch members. Therefore, the scope of the invention is indicated by the appended claims, rather than the foregoing description, and all changes which come within the meaning and range of equivalency of the claims are, therefore, intended to be embraced therein.

What is claimed is:

1. A cover for a laryngoscope, the laryngoscope having a generally elongated cylindrical handle, an insertion member having a curved end portion coupled to the handle, and a branch member branching out from an area between the handle and the insertion member, the cover comprising a single component having:

an end sheath for substantially covering the insertion member, the end sheath having a closed end portion for covering the curved end portion of the insertion member;

a generally Y-shaped branch-out section connected to the end sheath;

a first sleeve extending from the Y-shaped branch-out section for covering the branch member; and a second sleeve extending from the Y-shaped branch-out section for covering the handle, the second sleeve having an aperture for insertion of the laryngoscope into the cover wherein the aperture of the second sleeve forms an opening to access the interior of the end sheath, the Y-shaped branch-out section and the first sleeve.

2. A cover for a laryngoscope as defined in claim 1, wherein the Y-shaped branch-out section comprises a bellows.

3. A cover for a laryngoscope as defined in claim 1, wherein the Y-shaped branch-out section comprises an elastic material.

4. A cover for a laryngoscope as defined in claim 1, wherein the end sheath is configured to substantially conform to the exterior surface of the curved end portion of the laryngoscope.

5. A cover for a laryngoscope as defined in claim 1, wherein the end sheath is formed from a substantially transparent material.

6. A cover for a laryngoscope as defined in claim 1, wherein the end sheath, the Y-shaped branch-out section, the first sleeve and the second sleeve are formed from a substantially transparent, elastic material.

7. A cover for a laryngoscope as defined in claim 1, wherein the end sheath, the Y-shaped branch-out section, the first sleeve and the second sleeve substantially conform to the exterior surface of the laryngoscope.

8. A cover for a laryngoscope as defined in claim 1, wherein the first sleeve has an aperture for allowing connection of an external device to the branch member.

9. A cover for a laryngoscope, the laryngoscope having a generally elongated cylindrical handle, an insertion member having a curved end portion coupled to the handle, and a plurality of branch members branching out from an area between the handle and the insertion member, the cover comprising a single component having:

an end sheath for substantially covering the insertion member, the end sheath having a closed end portion for covering the curved end portion of the insertion member;

a branch-out section connecting to the end sheath;

a plurality of sleeves extending from the branch-out section for covering the respective plurality of branch members; and a main sleeve extending from the branch-out section for covering the handle, the main sleeve having an aperture for insertion of the laryngoscope into the cover wherein the aperture of the main sleeve forms an opening to access the interior of the end sheath, the branch-out section and the plurality of sleeves.

10. A cover for a laryngoscope as defined in claim 9, wherein the plurality of branch members comprise two branch members and the plurality of sleeves comprise two sleeves for covering the respective two branch members.

11. A cover for a laryngoscope as defined in claim 9, wherein the branch-out section comprises an elastic material.

12. A cover for a laryngoscope as defined in claim 9, wherein the end sheath is configured to substantially conform to the exterior surface of the curved end portion of the laryngoscope.

13. A cover for a laryngoscope as defined in claim 9, wherein the end sheath is formed from a substantially transparent material.

14. A cover for a laryngoscope as defined in claim 9, wherein the end sheath, the branch-out section, the plurality of sleeves and the main sleeve substantially conform to the exterior surface of the laryngoscope.

15. A cover for a laryngoscope as defined in claim 9, wherein at least one of the plurality of sleeves has an aperture for allowing coupling of an external device to at least one of the plurality of branch members.

16. A cover for a laryngoscope as defined in claim 9, wherein the end sheath, the plurality of sleeves, the branch-out section and the main sleeve are formed from a substantially transparent material.

17. A cover for a laryngoscope, the laryngoscope having a generally elongated cylindrical handle and an insertion member having a curved end portion coupled to the handle, the cover comprising a single component having:

a polyurethane end sheath for substantially covering the insertion member, the end sheath having a closed end portion for covering the curved end portion of the insertion member; and a polyurethane sleeve extending from the end sheath for covering the handle, the sleeve having an aperture for insertion of the laryngoscope into the cover wherein the cover is invertable through the aperture in the polyurethane sleeve, upon removal of the laryngoscope, such that all exterior, contaminated surfaces of the polyurethane end sheath and polyurethane sleeve are located in the interior of the inverted cover.

18. A cover for a laryngoscope as defined in claim 17, wherein the laryngoscope includes a generally Y-shaped branch-out section connecting to the end portion and a branch member branching out from an area between the handle and the insertion member, and wherein the cover further includes a polyurethane branch sleeve extending from Y-shaped branch-out section for covering the branch member.

19. A cover for a laryngoscope as defined in claim 17, wherein the polyurethane end sheath is formed of a polyurethane material, having a thickness ranging between approximately 1 mil. and approximately 2 mil.

20. A cover for a laryngoscope, the laryngoscope having a generally elongated cylindrical handle and an insertion member having a curved end portion coupled to the handle, the cover comprising a single component having:

an ethyl methyl acrylic end sheath for substantially covering the insertion member, the end sheath having a closed end portion for covering the curved end portion of the insertion member;

an ethyl methyl acrylic sleeve extending from the end sheath for covering the handle, the sleeve having an aperture for insertion of the laryngoscope into the cover wherein the cover is invertable through the aperture in the ethyl methyl acrylic sleeve, upon removal of the laryngoscope, such that all exterior, contaminated surfaces of the ethyl methyl acrylic end sheath and ethyl methyl acrylic sleeve are located in the interior of the inverted cover.

* * * * *